| United States Patent [19] | [11] | 4,394,312 |
|---|---|---|
| Han et al. | [45] | Jul. 19, 1983 |

[54] PROCESS FOR PREPARING RIFAMYCIN DERIVATIVES

[75] Inventors: Moon H. Han; Baik L. Seong, both of Seoul, Rep. of Korea

[73] Assignee: Korea Advanced Institute of Science and Technology, Seoul, Rep. of Korea

[21] Appl. No.: 373,807

[22] Filed: Apr. 30, 1982

[30] Foreign Application Priority Data

Oct. 15, 1981 [KR] Rep. of Korea ............ 3897/1981[U]

[51] Int. Cl.$^3$ .......................................... C07D 498/08
[52] U.S. Cl. .............................................. 260/239.3 P
[58] Field of Search .................................. 260/239.3 P

[56] References Cited

U.S. PATENT DOCUMENTS 3,644,337  2/1972  Bickel et al. ................. 260/239.3 P Primary Examiner—Robert T. Bond
Attorney, Agent, or Firm—Holman & Stern

[57] ABSTRACT

3-Dialkylaminomethyl derivatives of rifamycin S is provided by reacting rifamycin S with an iminium salt in an organic solvent. This compound is converted to 3-dialkylaminomethyl derivatives by virtue of ascorbic acid.

4 Claims, No Drawings

PROCESS FOR PREPARING RIFAMYCIN DERIVATIVES

FIELD OF THE INVENTION

The present invention relates to a process for preparing rifamycin derivatives, and more particularly relates to a process for preparing 3-dialkylaminomethyl derivatives of rifamycin S and rifamycin SV having the formula:

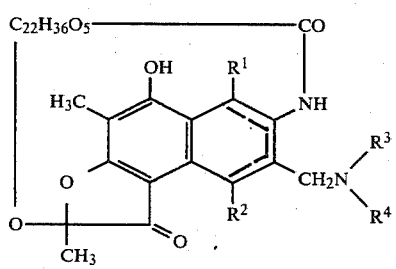

wherein $R^1$ and $R^2$ represent oxo (=O) or hydroxy (—OH); and $R^3$ and $R^4$ represent methyl, ethyl, propyl, isopropyl, butyl, or pentyl, or are connected by a methylene bridge where

is piperidine or 3-methylpyrrolidine, starting from rifamycin S.

BACKGROUND OF THE INVENTION

Rifamycins, which are a group of macrocylic hydroquinonequinone antibiotics having a close relationship to each other, are described in *Antibiotics Annual*, 262 (1959), *Appl. Microbiol.*, 9, 325 (1961), and *Progr. Ind. Microbiol.*, 6, 21 (1967).

Rifamycin derivatives have been prepared by the chemical conversion of rifamycin B, which is an antibiotic produced by fermenting *Nocardia mediterranei*. For example, a number of 3-dialkylaminomethyl derivatives of rifamycin SV can be produced by contacting rifamycin S with dialkylamine and formaldehyde (See, Maggi et al., *J. Med. Chem.* 8, 790 (1965)). This process is essentially based on the Mannich reaction which has widely been used in organic synthesis for the preparation of amino derivatives of the compounds containing active hydrogen atoms (See, Mannich et al., *Arch. Pharm.* 250, 647 (1912) and H. O. House, *Modern Synthetic Reactions* 2nd Ed., pp. 656, (1972), Benjamin Inc.). Under the usually slightly acidic reaction condition, the mechanism of the Mannich reaction is believed to involve electrophilic attack by an iminium salt on the active methylene compound (See, T. F. Cummings et al., *J. Org. Chem.*, 25, 419 (1960). The iminium salt is produced by condensation of alkylamine and formaldehyde as represented by the following equation:

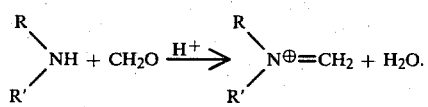

The amine may be of a primary or secondary one; however, a secondary amine is preferably used to avoid any undesirable side reactions. The yield of the Mannich derivatives may differ widely depending on the respective active methylene compounds. For the special case of rifamycins, it has been reported that the yield was about 5 to 72% (See, Maggi et al., *J. Med. Chem.*, 8, 790 (1965)).

Although the Mannich reaction has been previously applied to quinones and hydroquinones (Leffler, M. T. and Hathaway, J., *J. Am. Chem. Soc.*, 70, 3222 (1948)), in the case of the rifamycins only rifamycin S undergoes the Mannich reaction (Maggi et al., *J. Med Chem.*, 8, 790 (1965)). During the reaction, a certain amount of rifamycin SV and alkylaminomethyl rifamycin SV along with the alkylaminomethyl rifamycin S were observed due to the reducing property of the formaldehyde (Maggi et al., *J. Med Chem.*, 8, 790 (1965)). The relatively low yields of this reaction for the special case of rifamycins are, in large part, due to the formation of rifamycin SV which is an inactive form for this reaction. Furthermore, the excess of alkylamine or formaldehyde remaining in a free state may react with the rifamycin S molecule to form other side products. Therefore, in view of the unsatisfactory yield of the alkylaminomethyl rifamycin derivatives based on the Mannich reaction, we have now discovered that the use of pure iminium salt, instead of a mixture of alkylamine and formaldehyde, in obtaining alkylaminomethyl derivatives from rifamycin S results in a better yield.

SUMMARY OF THE INVENTION

It is the general object of the invention to provide a new process for preparing 3-dialkylaminomethyl derivatives of rifamycin S in a high yield.

It is another object of the invention to provide a new process for preparing 3-dialkylaminomethyl derivatives of rifamycin SV from rifamycin S in a high yield.

These and other objects can be attained by the process of the invention which comprises contacting rifamycin S with 1.0 to 1.5 equimolar amount of iminium salt obtained by the acidic cleavage of aminal in a suitable organic solvent at a temperature ranging from room temperature to the boiling point of the solvent for a time sufficient to complete the reaction or, if necessary, treating the resulting compound with ascorbic acid.

The term "suitable organic solvent" as used herein refers to a solvent or solvent mixture in which both rifamycin S and the iminium salt show satisfactory solubility and in which the reaction will occur while the formation of impurities is inhibited. Suitable solvents useful in the process of the invention include, but are not limited to, tetrahydrofuran, dioxane, ethylacetate, benzene, acetonitrile, chloroform, methylene chloride, methanol, ethanol, propanol and the like. Among these acetonitrile gives the highest yield in a short reaction time. Alcohols usually give a poor yield. The duration of the reaction depends upon the temperature selected from the range of about 20° C. to the boiling point of the solvent used. A lower temperature results in a longer reaction time. Generally, a period of reaction time of about 2 to about 6 hours gives the best results. The extent of the reaction can be followed by a thin layer chromatography (TLC) using Eastman chromagram sheet No. 13181 and a developing solvent of chloroform:acetone (1:1) mixture. The reaction may further be followed by reduction with ascorbic acid. Without reduction, the end point of the reaction is confirmed by the disappearance of rifamycin S spot (purple, $R_f=0.5$). With reduction, the end point is the disappearance of rifamycin SV spot (yellow, $R_f=0.2$) to dialkylaminomethyl rifamycin SV spot (deep yellow, $R_f=0.6$).

The reduction of the quinonoid moiety of rifamycin S to the hydroquinone form of rifamycin SV is described in detail in Japanese Laid-Open Patent Publication No. 38-4852 (1964). After the reaction is terminated, the reaction solution is washed with the same volume of water to remove the excess of iminium salt. If the solvent is water-miscible, about 3 to 4 fold volume of water is added and the resulting products are extracted with a water-immiscible solvent.

If an ascorbic acid solution (1–5%) is used in the washing step, 3-dialkylaminomethyl rifamycin SV can be obtained. After concentration of the organic layer, crystals of 3-dialkylaminomethyl derivatives of rifamycin S or rifamycin SV can be obtained, respectively. The yields are in the range of 80–95%. The iminium salt for use in the process of the invention is usually prepared in a highly purified form by the acidic cleavage of aminals such for example as N,N,N′,N′-tetraalkylmethylenediamine following the reaction:

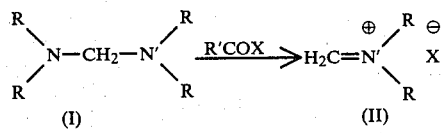

The iminium salt (II), called N,N-dialkyl(methylene)ammonium halide, is prepared by the reaction of an aminal (I) and an acid halide in the presence of an organic solvent. Acetyl chloride or benzoyl chloride is usually used as a source of an acid halide. Ethers are preferred as a solvent although other solvents may be used. The iminium salt is usually obtained as a white precipitate and can be used without further purification. The iminium salt also can be stored indefinitely in an anhydrous condition (See, Böhme et al., Chem. Ber. Jahrg. 93, 1305 (1960)).

The acidic cleavage of aminals is in general carried out under a stream of dry nitrogen gas using an apparatus with ground joint of fritted sintered glass which has carefully been dried to prevent the admission of external air. The white precipitate is collected by streaming off the reaction solution followed by a wash with the same solvent in order to eliminate undesirable by-products, carboxylic acid and dialkylamine.

After drying, it can be preserved for six months or more. The only precaution during the process is to exclude atmospheric moisture therefrom.

In practising the process of the invention, it is also possible to employ the iminium salts in a purified form obtained from other routes.

According to the invention, to rifamycin S in a suitable solvent, a slightly excess amount of an iminium salt in a molar basis (about 1.0–1.5 fold) is added. The reaction is typically carried out in a three necked flask equiped with a reflux condenser and an agitation system.

DETAILED EMBODIMENTS OF THE INVENTION

The following examples will further illustrate the present invention.

EXAMPLE 1

To 3.2 grams of N,N,N′,N′-tetraethylmethylenediamine in 40 ml of absolute ether, 3.0 grams of benzoyl chloride were added dropwise at room temperature for 5 minutes with light agitation. After filtering, the resulting precipitate was washed with 40 ml of ether. After drying at 50° C. for 1 hour, 2.2 grams of N,N-diethyl(methylene)ammonium chloride were obtained. 7 Grams of rifamycin S were dissolved in 200 ml of acetonitrile, and 1.3 grams of iminium salt as prepared above were added thereto and the reaction solution was stirred for 2 hours at 40° C. Additional iminium salt was added if unreacted rifamycin S was remained as demonstrated by silica gel thin layer chromatography with a developing solvent of acetone:chloroform (1:1). The end point was confirmed by the complete disappearance of rifamycin S spot (purple, $R_f=0.5$). After the reaction was completed, the solution was concentrated to 50 ml at 40° C. To this, 300 ml of distilled water was added. After extraction with 200 ml of ethylacetate, the organic layer was separated and concentrated to 50 ml at 40° C. The product gradually crystallized during concentration. After chilling for one day at $-20°$ C., 7.0 grams of needle shaped crystals of purple color were obtained. By the similar procedure, additional 0.2 gram of crystal was obtained from the mother liquor (Yield=93%). This compound has the following partial formula:

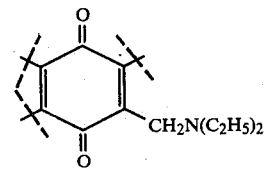

The elemental analysis confirmed the chemical structure. The molecular formula was $C_{42}H_{56}N_2O_{12}$ as evidenced by elemental analysis (C, 64.2%; H, 7.6%; O, 25.1%, N, 3.1%).

EXAMPLE 2

To 10.2 grams of N,N,N′,N′-tetramethylmethylenediamine in 150 ml of absolute ether, 8.6 grams of acetyl chloride were added dropwise at room temperature for 5 minutes with light agitation. The white precipitate obtained after filtration was washed with 100 ml of absolute ether and dried at 50° C. for 1 hour. 9.2 grams of N,N-dimethyl(methylene)ammonium chloride were obtained. After 7 grams of rifamycin S were dissolved in 150 ml of benzene, 1.2 grams of N,N-dimethyl(methylene)ammonium chloride were added. During reaction with refluxing and stirring, the extent of reaction was continuously monitored by thin layer chromatography. After 3.5 hours of reaction, the solution was poured into 200 ml of an ascorbic acid (3% w/v) solution and vigorously agitated. The quinonoid moiety of the product was reduced to the hydroquinone form by this treatment as indicated by the gradual disappearance of 3-dimethylaminomethyl rifamycin S spot (purplish brown, $R_f=0.5$) accompanying the gradual intensification of 3-dimethylaminomethyl rifamycin SV spot (deep yellow, $R_f=0.6$) in thin layer chromatography, using developing solvent of chloroform:acetone (1:1). After the reduction was completed, the organic layer was separated and evaporated to dryness. After solubilization in 100 ml of ethylacetate at 60° C., it was concentrated to 40 ml and chilled at −20° C. for one day. The brownish yellow crystals were recovered and dried over sodium sulfate. When additional crystals were recovered from the mother liquor, the total weight was 6.9 grams (Yield=91%). This compound has the following partial formula:

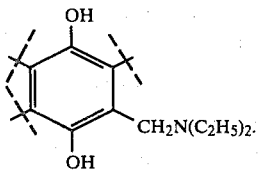

The molecular formula was $C_{40}H_{54}N_2O_{12}$ by elemental analysis (C, 64.0%, H, 8.1%, O, 24.9%; N, 3.0%).

EXAMPLE 3

1.7 Grams of acetyl chloride were added dropwise to 3.6 grams of dipiperidinomethane in 40 ml of absolute ether at room temperature for 5 minutes with light agitation. The resulting precipitate was filtered and washed with 40 ml of ether. After drying over sodium sulfate, 2.4 grams of N-chloromethyl piperidine were obtained. 2 grams of N-chloromethyl piperidine were added to 10 grams of rifamycin S dissolved in 300 ml of a chloroform:acetonitrile (1:1) mixture. After reaction for 6 hours at room temperature, the solution was washed with 500 ml of a 2% ascorbic acid solution. The water layer was extracted again with 50 ml of chloroform. The chloroform layer was separated and concentrated to 50 ml. To this, 200 ml of petroleum ether was added dropwise for 10 minutes. The amorphous crystals of 3-piperidinomethyl rifamycin SV with brown color were formed. After filtration, and drying over sodium sulfate, 11.2 grams of the crude product were obtained. By recrystallization, rifamycin SV crystals were obtained (yield 85%). The elemental analysis confirmed the chemical structure of the compound as the following partial formula:

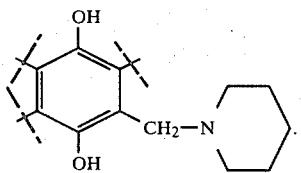

The molecular formula was $C_{42}H_{56}N_2O_{12}$ determined by elemental analysis (C, 62.9% H, 7.8%; O, 26.0%; N, 3.3%).

EXAMPLE 4

2.5 Grams of N,N-dipropyl(methylene)ammonium chloride prepared from N,N,N',N'-tetrapropylmethylenediamine by the procedure similar to that described in Example 1 were added to 7.5 grams of rifamycin S dissolved in 150 ml of tetrahydrofuran. After reaction at 60° C. for 2 hours, the reaction mixture was concentrated to 50 ml and poured into 300 ml of a 2% ascorbic acid solution. After extraction with 400 ml of ethylacetate, the organic layer was separated and concentrated to 50 ml. By chilling at −20° C. for one day, 7.2 grams of 3-dipropylaminomethyl rifamycin SV were obtained (Yield=83%). The molecular formula was $C_{44}H_{62}N_2O_{12}$ by elemental analysis (C, 65.2%; H, 8.0%; O, 23.6%; N, 3.2%).

EXAMPLE 5

3 Grams of N,N-dibutyl(methylene)ammonium chloride obtained from N,N,N',N'-tetrabutylmethylenediamine were reacted with rifamycin S by the same procedure as described in Example 1 to yield 7.6 grams of 3-dibutylaminomethyl rifamycin S (yield=84%). The molecular formula was $C_{46}H_{64}N_2O_{12}$ by elemental analysis (C, 66.0% H, 7.8%; O, 22.9%; N, 3.5%).

EXAMPLE 6

3 Grams of N,N-dipentyl(methylene)ammonium chloride obtained from N,N,N',N'-tetrapentylmethylenediamine were reacted with rifamycin S by the same procedure as described in Example 1 to yield 8.1 grams of 3-dipentylaminomethyl rifamycin SV (yield=93%). The molecular formula was $C_{48}H_{70}N_2O_{12}$ by elemental analysis (C, 66.5%; H, 7.9%; O, 22.4%; N, 3.2%).

EXAMPLE 7

5 Grams of N,N-diisopropyl(methylene)ammonium chloride prepared by the acidic cleavage of N,N,N',N'-tetraisopropylmethylenediamine by the procedure similar to that described in Example 1 were added to 15 grams of rifamycin S dissolved in 300 ml of acetonitrile. After reaction for 3 hours at 50° C., it was concentrated to 70 ml and poured into 50 ml of ethylacetate, and concentrated to 80 ml. Chilling at −20° C. for one day gave 14.4 grams of 3-diisopropylaminomethyl rifamycin SV crystals (yield=83%). The molecular formula was $C_{44}H_{62}N_2O_{16}$ by elemental analysis, confirming the chemical structure of the compound (C, 64.8%; H, 8.1%; O, 24.1%; N, 3.0%).

EXAMPLE 8

4.5 Grams of N-chloromethyl-3-methylpyrrolidine were prepared by the acidic cleavage of 6.0 grams of di-(3-methylpyrollidine)methane by the procedure similar to that described in Example 1. 3 grams of N-chloromethyl-3-methylpyrollidine were added to 10 Grams of rifamycin S dissolved in 240 ml of ethylacetate. After reaction for 2 hours at 40° C., the reaction mixture was added to 200 ml of a 3% ascorbic acid solution and vigorously agitated. The organic layer was separated and concentrated to 60 ml. After chilling for one day at −20° C. and then filtering, 10.6 grams of brownish yellow crystals of 3-(3-methylpyrollidinomethyl)rifamycin SV were obtained (yield=93%). The elemental analysis confirmed the chemical structure. The molecular formula was $C_{42}H_{56}N_2O_{12}$ (C, 63.1%; H, 7.6%; O, 25.5% N, 3.8%).

What is claimed is:

1. A process for preparing 3-dialkylaminomethyl rifamycin S derivatives having the formula:

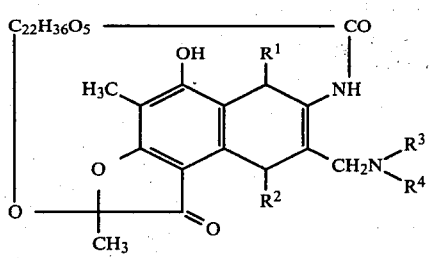

wherein $R^1$ and $R^2$ are oxo (=O); and $R^3$ and $R^4$ are methyl, ethyl, propyl, isopropyl, butyl or pentyl, or are connected by methylene bridge where

represents piperidine or 3-methylpyrrolidine which process comprises contacting rifamycin S with 1 to 1.5 equimolar amount of an appropriate iminium salt in an organic solvent at a temperature ranging from room temperature to the boiling point of the solvent for a time sufficient to complete the reaction.

2. The process of claim 1 wherein said solvent is one selected from the group consisting of tetrahydrofuran, dioxane, ethylacetate, benzene, acetonitrile, chloroform, methylene chloride, methanol, ethanol and propanol, and a mixture thereof.

3. The process of claim 1 wherein said solvent is acetonitrile.

4. The process of claim 1 wherein the reaction is carried out in two to six hours.

* * * * *